United States Patent
Ueyama et al.

(10) Patent No.: US 6,265,568 B1
(45) Date of Patent: Jul. 24, 2001

(54) **PROBES FOR THE DIAGNOSIS OF INFECTIONS CAUSED BY *BACTEROIDES FRAGILIS***

(75) Inventors: Hiroshi Ueyama, Osakak; Kanako Abe, Yawata; Hiroyuki Keshi; Akio Matsuhisa, both of Osaka, all of (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 09/381,849

(22) PCT Filed: Mar. 23, 1998

(86) PCT No.: PCT/JP98/01287
  § 371 Date: Jan. 11, 2000
  § 102(e) Date: Jan. 11, 2000

(87) PCT Pub. No.: WO98/42844
  PCT Pub. Date: Oct. 1, 1998

(30) Foreign Application Priority Data

Mar. 25, 1997 (JP) .................................................... 9-071079

(51) Int. Cl.⁷ .............................. C07H 21/04; C12Q 1/68
(52) U.S. Cl. ................... 536/24.32; 536/24.3; 536/23.1; 435/6
(58) Field of Search .................................. 435/6; 536/24.3, 536/23.1, 24.32

(56) References Cited

U.S. PATENT DOCUMENTS 5,571,693 * 11/1996 Rasmussen et al. ................ 435/69.1

OTHER PUBLICATIONS

Novicki, T.J. et al., "Characterization and DNA Sequence of the Mobilization Region of pLV22a from *Bacteroides fragilis*," *J. Bacteriol.*, 177(15):4466–4473 (1995).

PCT International Preliminary Examination Report, International Application No. PCT/JP98/01287, filed Mar. 23, 1998, dated Feb. 14, 2000.

\* cited by examiner

*Primary Examiner*—W. Gary Jones
*Assistant Examiner*—Jeanine Golderg
(74) *Attorney, Agent, or Firm*—Marshall, O'Toole Gerstein, Murray & Borun (57) ABSTRACT

The DNA from the bacteria *Bactereoides fragilis* is extracted, then completely digested with restriction enzyme HindIII, followed by cloning into a suitable vector to select a probe comprising DNA which is essentially contained in *Bacteroides fragilis,* then the sequence of the probe is elucidated.

20 Claims, 1 Drawing Sheet

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 2184 base pairs
      (B) TYPE: nucleic acid
      (C) STRANDEDNESS: double
      (D) TOPOLOGY: linear    (ii) MOLECULE TYPE: DNA (genomic)

(vi) ORIGINAL SOURCE:
      (A) ORGANISM: Bacteroides fragilis
      (B) STRAIN: Clinical Isolate BF-7

(xi) SEQUENCE DESCRIPTION: SEQ ID NO: 1:

```
AAGCTTCTAC ACGCTTCAAT TCTTGAAACA CAAGTTCTAC CGCAAGCTGC GGATTTACTT      60

TGGGCGTGGT GTCCTTTCTC TTTCGGGGGC TGTACTGCCC CTGCTTATAG GTGTAATCCT     120

CCGTCTTTGG GTTTGAGGGT GTTTCCATAA TTCCTGCTGA TTGAGTTATA CTTCAATTTT     180

TTCTGTGTCT TCTCGATATG GGCAAGCGTA TAGCCTTTCC CTATCTCGCT TGCCTTGTAT     240

TCCGTTCCGC TCCGGGCTTT CACGTAGTAG CCGTTGAGTT TGCCTGTACT TGCCCGGGCT     300

TCCCTTACCT TGAAGCCCAG TTTTCCGAGT TCCCGGCTGA ATCCGGCAAG GTCAAACCCC     360

TGCATCCGTA TAAGAACATC ATCCATAGCC TGTTTTATCT CTTCCCTGTT GGCTTTGCCT     420

ATATCCTTTG ACTGTACCAA GTTCCGTTCT CTGGCTATAC TGTTGGCAGC TTCCGTAGCT     480

CTCTTCCCTA TCCAGTTATC CTGGTATAGT TCTCCCGATA ACGACACACG GTTTGCCAGT     540

ATATGCAGGT GGGCTTGCCT GCGGTTCTTC TCCGTTCCGC TGTGCTTCAC AATGATGTAC     600

TGGTGGTTCA TCAAACCCAT GCGCTGCATG AAGTCATTAC CGAGCTTCGC CCAGTCCGCA     660

TCGGTCATGC CTGCACTTTC TTCCACTGAA GGGCTGACCT CAAACCGAAG CAGTTGTTCT     720

TTACGTTCGG AAAATCAACA AAGTAAGGTT TCATCTCCTG CACCATATCT TCGCCTGTGC     780

AGCCGAAAAG CTCATGGCGG TGTATCTCGG TGGCTGCTGC CTCTCCGTTT ATCTCTTTGG     840

CAAGGTCGTA CTCCAGTGCT GCCGTGCCAT GAGATATGCT CTTTCCTTTT GCTATCATCG     900

TGAAAGTATC TTTTTAAGTT CATTGATTAG TGCCTGGTTC TCCTCGAACA CTTCCCTGTA     960

CTGGCGCCCA CCGAAGTAGT TGTTCAGACG CTGGAGTGTT CCTTTCAGTC GGGCTATCTC    1020
```

-continued

```
CCGAAACAGT TCCCTTTCTT CTTCCGTGTA CCTCTCCTTG GGTCGTCCGC CCAGTGCGAG      1080

TGTACGGCAG TACTCCGATA TGCTGATGCC GCATCGGGCT GCCTGTTCCG CAAGTGCCGC      1140

CTTTTCAAGT GCGGTGCAGC GGAATGTTAT CTTCTCCGTT CGATTTACTT TCATGTCGCA      1200

AAGGTAATCT TAAAATTCTT TTGAGCAAAG CGAGAAAGGC AAGAATGTCC GACAAGGACA      1260

CTTCTTGCTA TATATACACA TTCCGCATGG GAATACACAC AGCGCTAACA CACTGCATAG      1320

CCACACACTT TTTTTTCTTT TTCCCTGCCA TTTCCACAAC GGAACACGGA GAGCGGTCAA      1380

GGGTTCGAGC GGAAAAAACC GCACAGCTTC ACTGTGCGGT TTTTTCCGCT CCGAACTTGC      1440

GAAGCCCTTG ACGGCTTCGG AGTGTGGAGT TACCTTTGCA GACCGAAAAG AGAAAAAACA      1500

CAGTTTCGCT TCACTAACGC TGACTGGTCA AGGATACCC TGTTCAGATA TGATTTTTTT      1560

AAGAATAGAT ACACTTACGG TAGAGAAGTC TGACTTATCA TAGACATCCA CAAGATAAAC      1620

ACGACCTTCA CTCTCCGATG CACAAATCGT GTATGTGATA ACACGTGCTC CCCCAGACTT      1680

ACCCTTTCCC TTAGAAACAA TGGCAAGTCT TATTTTACGG ATACCAGGGC TTAGTTCATC      1740

CCCCTGCATG GGGTTCTTTT CCAATGACTC GATAAAATCC TTCATGTCAG CCTTAAAAGA      1800

CTTATACCTT TTTGCAAGGA TTTTCGCTTC CCTCTCAAAA TGTGGGGTGG TCTTTACTTC      1860

AAAGCTCATC AAGAAATGCG TTTGCGCTCT TGGCTGGCTG CTCACCAGCT TCGATTCGTT      1920

TCACTTCATT CAAGCCCTCT CTTATTCGAG TGGCTATTTT TCTTCTACG GACACTGGCA      1980

CCAATTTAAA ATCACCGATA CGTGAAGTCA GAAAGACGGA TTCTCCCTGA ATAGCACGAA      2040

GAAGGGTCGC TGTCTGATTC GTCCGAAATT TGCTCAATGG AATTACTTGC ATATATCTTA      2100

AACTTTTTGA TTGTGATACA AATGTAACCA TTGTCACCGA TATTGTAACC AAATTAATAT      2160

ACTTTAACAC GCAAAAAAAA GCTT                                            2184
```

(2) INFORMATION FOR SEQ ID NO: 2:

(i) SEQUENCE CHARACTERISTICS:
        (A) LENGTH: 2163 base pairs
        (B) TYPE: nucleic acid
        (C) STRANDEDNESS: double
        (D) TOPOLOGY: linear     (ii) MOLECULE TYPE: DNA (genomic)

(vi) ORIGINAL SOURCE:
        (A) ORGANISM: Bacteroides fragilis
        (B) STRAIN: Clinical Isolate BF-17

(xi) SEQUENCE DESCRIPTION: SEQ ID NO: 2:

```
AAGCTTACGG CAGCGGGCGG CGCTACTCCT TTCTTCTGCA CGACTGCTTC CGGATCCGGA        60

TCGGCCGGCA CGATGTCCCT GACGGATGGC GCTTTGTCCG GACTGGCCGC GGTGGGTGAA       120

ATCTCTTTTA CCCCATCGGC CCGTCCGCAA CAGGTCGGCA CCTCGGGCCC CGTTACAGTG       180

GCCTACGGGC TGGTGGCTCC GAAGCTGAGG CGGCTTCGGG CATGCGGGTG ACGTTGACGC       240

TGACACTGGG TGAACAAAGC TCGGACGCTA CCGAACGGGA TCTTACCCTC TCGACCGATG       300

CCTTCAACCC GGCATGGCAG AAAGGATACC GCTACGTCTA TACCTTGACG CTCGGCGAAC       360

GGGGAATCAG CCTGCAACCT GTCGATATAA AAGGGTGGAC GGAAGTTTCC GAGGAGAGCA       420

GTGACGTAGA TCCCGGCTGG CAATGAAACA ATGATTCAG AATGACAAAT GATTCAGAAC       480

AATAAATGGT TCAGAATGAC AAATGGTTCA GAATGACAAA TGACAAATGA TTCAGAATGA       540

ATGATTCAGT ATGAAAACAG ATAGATTATA CCAAACGGTT TTAGGCTGCC TGCTGCTTAC       600

CGCAGTTGTT CGGACAATGC GCTGACCCCT TCGTTGCCCG AAGACCTCCG CTTACGGTGT       660
```

```
CCGCCGCGAT CTGCGCTTCC GGTGAAGGCC GGGAGTCTGA GACCCGGGCG GCCGTGGCAG    720

CCGGGACCCG TGCCGTGGCA GCCGACAACG GTTACGACCG CAGCACCTTT GCCGCAGTGA    780

CAAAATCCGT ATCATCCGCT CGCGGAACGG CTCGTCATCC ACTCCGGTGG ACTATATATT    840

GAACTCCGCT TCTTCCGGCA ACAGTACGGG CGAGTGGAAA CCTTCGGTGA CGGGTACGGA    900

GCTGCTCGTT GAATCCGGTG CCACCTACCA GGCGAGTTAC CCTATCGAAT ACTCGGGTAT    960

CCGTGCCGAC CAGCGAAAGG CGGGAGGTGA GGACTACCGC CTGAGCAATC TGCTGGAGAC   1020

TCCTGAGAAG GTGGCGATCG GCCGTGACGG AACCCTCTCC TTTACAGGCG AAAGCCCTTT   1080

GTGCACAAAG GCGTGAAGCT GACCCTGAAA TTTTCGAGAA AGCATACACT GTCCAAGGAT   1140

TTTACGAGTA TGACCGTAAC CGGGAATGGG CTTTACTCCG GAGAAGCAAG CAAGGATGAA   1200

ACCGTCTACC TGTATCACCC CGGCGGTACA GACAAAGAGC AATATACCTG GCATGGCATT   1260

ATCGCCCCGC TTACCTTCCC AACAGTCGAT ACAGGTATCG GTGACGGATG CTAACGGAGT   1320

GGTCTATGAC GTCACCCTTA TTTGCGCAAG GGCGGCGAAC AGTCACTACA CCTATACGCT   1380

CACCCTGAAA AATGATGTGC TGGTTCCCAC CGGTCAGGAG ATCAAAGAGT GGCAAAGCGG   1440

GGATTCGCAT ACAGGAACCT TAAGTTGATG TAACTTAGTT TGATGTAATA TTAGTTGATG   1500

TAATATTAGT TTGATGTAAC CCCATGAAAA AGAAAAAGAA TAGAATCCTA TCGGTATCCG   1560

GCGCGGCTCT CTGCCTGTTC TTCCCGGTTC TGCTGGCCGC CTGCTCGCAA GAGGATGCTT   1620

TGCCCCGTCC GTTGGAAGTA TCGGCGGAGG TGGGGAATCC CGCTACCCGT GCGGCGGCAG   1680

ACTCGCATGC CGATGATTAT GATAAAAGTG AATTTGTAGC GGGTGATGTC ATCCGGATTA   1740

CGGACGGCAC GAAAACTGCC GACTACCAAC GGGTGGTCAC CGGCACAACC GGCACCTGGC   1800

AACCCGCAAG CGGACAAACA GCGCTCACCA CCACCGGTAG TGAAACGTTT ACGGCTTCGT   1860

ATCTACGGCG TTCACCCGGA TTCTAACCGA TCAGCGCACA GCCACCAATT TCTGGCAAAG   1920

CAACCAGCTG ACGGCTAAAG GAGTACTCGA TGGCAATAAG GCTACGTTCT CGTTCGCTCC   1980

GGAAGCGGCG AAGGTGACCT TGGTGGTGAA GTATGGAAAT AGTGATAGTG ACAAGAAGCT   2040

TCATTATGGC CAACAACGTT CCTGTTGTTT TAGACAGAGA AGCCAAATCA TAAATATCCG   2100

TCGGCTTCAC TTTCTCGCTA TTTGCATCTG TATGGTATCC GAAGCACCGG TCATACAAAG   2160

CTT                                                                2163
```

(2) INFORMATION FOR SEQ ID NO: 3:

(i) SEQUENCE CHARACTERISTICS:
  (A) LENGTH: 1657 base pairs
  (B) TYPE: nucleic acid
  (C) STRANDEDNESS: double
  (D) TOPOLOGY: linear  (ii) MOLECULE TYPE: DNA (genomic)

(vi) ORIGINAL SOURCE:
  (A) ORGANISM: Bacteroides fragilis
  (B) STRAIN: Clinical Isolate BF-21

(xi) SEQUENCE DESCRIPTION: SEQ ID NO: 3:

```
AAGCTTATCT TATGGACCGT ACCCGAAGGA GAATTGCTTG AAGAAGCGAT TGAATGGTGC     60

CGCCAACGGG GAGTCTTTTT CTATTCTGTC AACAAGGACT ATCCGGAAGA AGAAAAGAGT    120

CATAACGGAT TCTCCCGTAA ACTGAAAGCA GACCTGTTTA TTGATGACCG GAACCTGGGA    180

GGTTTGCCTG ACTGGGGAAC CATCTACCAG ATGATCCATG AACAAAAGCC ATACGAACCT    240

GTTCTATGTG ACAGGCAGAA ACCGACCGGC GATTTAAGCT GGATAGAGAA ACTGCTCGGC    300
```

```
AAACGTAACA AATAAAGAAA GAGGTTGACA ATGAACAATC ATGTAGTAAT TATGGCCGGT      360

GGCATAGGAA GTCGATTTTG GCCCATGAGT ACACCGGAAT GTCCCAAACA ATTCATAGAT      420

ATATTGGGAT GTGGAAAAAC ACTGATTCAG CTAACTGTAG AGAGATTCGG TAATGTTTGT      480

CCACAGGAGA ACATGTGGGT GGTCACTTCG GAAAAGTATA GAGATACTAT TCGGGAGCAA      540

CTGCCGGGTA TCCCGGAAAG TAATATACTG GCAGAACCCT GTCCCAGAAA TACAGCTCCC      600

TGCATTGCGT ATGCCTGCTG GAAAATAAAA AGAAATATC CGGAAGCCAA CATTGTCGTG       660

ACTCCTTCCG ATCAAGTGGT AATCGATACC ACTGAATTTC GCAGGGTGAT TGAGAAAGCG      720

CTTTTGTTCA CTGATAAAAG CAGTGCTATC ATCACATTGG AATAAAACC CGCCCGTCCG       780

GAAACCGGAT ATGGATATAT CGCCGCAGGT GAACCGATAA CGAGAGACAA AGAAATATTC      840

CACGTAGAAG CATTCAAGGA AAAGCCTGAT AAAGAAACTG CTGAAAAATA TCTGGCAGCA      900

GGCAACTACT TCTGGAATGC AGGAATATTC GTTTGGAATG TGAGAACGAT CACAGCCGTA      960

ATGCGGGTAT ATGCACCGGG GATAGCTCAG ATTTTCGACC GGATATATCC CGACTTTTAT     1020

ACAGAACGCG AGGAAGAAAG TGTGAAGAAG CTATTCCCCA CTGCCGAAAG TATCTCGATA     1080

GATTATGCAG TGATGGAAAA AGCGGAAGAG ATTTATGTAT TACCTGCCCA AATGGGGTGG     1140

TCGGACTTAG GTACCTGGGG AGCATTACAC ACCTTGTTGC CAAAAGATAA AGAAGGAAAT     1200

GCAACAGTAG GACCGGATAT CCGGATGTAT GAAAGTCGAA ACTGCATGGT GCATGCCTCA     1260

CAGGAAAAAC GAGTAGTCAT ACAAGGGCTG AACGATTACA TCATAGCCGA AAAAGACAAT     1320

ATATTATTAA TATGCCAGTT ATCAGAAGAG CAACGAATTA AGATTTCTC AAAAGAATAA      1380

ATGTTGATCC CTTTCAATAT TTATAAATCC CGGTTATAAT ACCGGGTGTA GGGGCGTCCC     1440

GATGCGAATC GTGACTGCTT TTATTTGTTT TGTTTGTGTG TGTTCCTCCG GCCAGGCGTG     1500

GTCGGAGGAA CATTTTTTTA TGCCCGTATT CTACAACTTG TGATTCAAGA TCCAATCCGA     1560

AAATTTCTTT AAAGACTATC TCGTCCAAGT CACCAATCTC AACCTTAAAA TGAAAGATTC     1620

ATACCAAATG TTTCAACGAT AAAGTATAAA AAAGCTT                              1657

(2) INFORMATION FOR SEQ ID NO: 4:

(i) SEQUENCE CHARACTERISTICS:
            (A) LENGTH: 2079 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Bacteroides fragilis
            (B) STRAIN: Clinical Isolate BF-28

(xi) SEQUENCE DESCRIPTION: SEQ ID NO: 4:

AAGCTTTCCT TTCCTATCGT ATTTAAAAAC TCCTGCATCA CTACCGGCCA ATACGAAAAT       60

ATAGTCTTTA GTCACTGCCA TACTGAGTAT ACTGGCACGA ACCGGCAATT TCACAAAATT      120

ATCCAACTGG ACATACGAGA TGCTATCTAC CAATTCCTTC ACTGAGATGG AGTCCTCTCT      180

ATCTAAAACA CTGGTCATCT CAACAATCGG ACAATCAGAT GGCACCTGAG CTAACAAATC      240

AATCTTCTCT GAACGGGAAG AAGAGCAACC GATCAGATGC GTCAATATAC CACAATATAA      300

AACTAATCTA ATCTTGTTCA TTTTGATTTT ATATTTAAAT AAAAGTCCAA CATCTTATTT      360

CTAAATAAGT CAAAACCATA TAATTGTATA TACCGATTAA CCAATAATC TTTAATACTT       420

TTTTTTTCTA ACAAATTCAT ACTCAAAGCA GTTATCATCT GCTGTGCTAA TATCTCAACA      480
```

```
TTAATAGAAC AAATCTCTTC CTGAGATATA TTAACTCTAA AAGGATAAGA TGGTCCAACC    540

ATTTCATTTA CTCCTGCTAC AGAAGTTGCT ACCAAAGGAA TTCCTCTCAT CATCATTTCA    600

ATCATTACAT AACTACATTG TTCTGTATAT GAAGCAATAA CCCCTAAGTC AGCCATAGAA    660

TAAATACAAT CCAATTTATC TTTCTCAACT CTACCAACAA ACGAAACTTT ATGCCATATT    720

CTTTCACACA GTTTCAAGTA AGTAGCGAAT TCACCATCTC CAACAATGAC TAAACGTACA    780

TTCTGTATTT TATCCTGTAC CATGCGAAAG GCTCGCAATA GTTCTTCTAT CCCTTTATTA    840

TGATCCAAGC GTCCTACAAA TAATATCAAA ATTTCTTTTT TACCTAGAAC CGGCTCCTTT    900

TCACATTCAT TATCTTGAAC AGATAGCTTA TGTGGCAAGC CATTTGCTAT ATATTTGAGT    960

TTAGCTATAG GGACTTGATA ATCATTTATC AGAATCTCTT TAGTACTTTT TGAAAGACAA   1020

ATAACATAGT CAACATAATT AAACATTTCT TTCTCAACCG TAAATGCATC AAACACATCT   1080

ATTTCCTTCA AACTCCTTTT GGTCGCATCT TGAGATAAAA TAAATGGAA ATAAGTCCTA    1140

TTTCCCTTTA AAACAAAACA CCAATTAAGA TAATGCACGG TAAAACAAAC CACACATCTT   1200

ATCTGCCTGC TCCTCAATGA TCTTACAATT GCCACATCTT GGTAAAAATT CAAATGAAAT   1260

ACATTAATAT TAAATAAATC AATATACTCC TGAAGGATAT ATGATATATT TCGACAGTAC   1320

CTTTCATACA AAAAGAATT ATCTTGAACA TCAACACTAG GAATAAGAAA TAGCCTTATA    1380

CCATTATTGG TTCTCATTTC AATATTTTCA ACATTTGCAC AAATCTGGAC TATTGTTAAA   1440

TTTAAGTCCG CACGTTCTCT TACCACTTTT GTCAACTGTT CAACATATGT TCCTACACCA   1500

TATTGTGAAG CTACACTTGA ATTATTAACG ATATAAATAT TCCTCATATC GAAGATTGAT   1560

CCCAAATTAT TTTTAATCCT TTTTTCCAAG ACAAATTATT ATCGCCATCA CTCCCTCTTA   1620

TGATCTCTGC CTGTATCTGT TGTATAGAAT AATTCACAGG ACAAGCTACA CATAATGCTT   1680

GAAGAAAAGC CGTATCAAAA AACGACTCTC TACCTATATC CAGTACTAAA CGAATACGTA   1740

TATATGAAGC TATACCAAGC AAGCCTGTTT CCAGAGAATG ATTATTCATT TTTTAAAAGA   1800

TTGTATTCCA ACAGCTTATT ATCAAGAGAT TTTAAAACGT CATCCACATT TCCATCTACA   1860

AATTTTTGCT GAAACAGATA TACTATTCCC CACCCAATGC CACATAAGCC ATCCGCAAAG   1920

TAAATCGGTA TATCTTCATG AACATCTTCA AAAACCTCAT CCAATAATTC ACCAGCAAAT   1980

TCCTCATATA AAGGGTTTTG TATATAACGG CTATAATGAA AGAAAAACAA GACAAGTCCC   2040

ATCTTGCCAT TAAAAAGTCC CAAACTTGGA AGGAAGCTT                         2079

(2) INFORMATION FOR SEQ ID NO: 5:

(i) SEQUENCE CHARACTERISTICS:
        (A) LENGTH: 1847 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Bacteroides fragilis
        (B) STRAIN: Clinical Isolate BF-34

(xi) SEQUENCE DESCRIPTION: SEQ ID NO: 5:

AAGCTTATAA AGAAGATTAT ATCCAACGAT TATTCGTCTT TAAAATTATG GATTGGAGCT     60

GATGAATTCA AGGAATTGCT TTATCTGAAT CAGGAAGGCG GTTCAGAGGG CACTACAGAA    120

GTCTATGATT ATGATGGTAA CTATCAAGGA AATATTGCTG AATTGTATAA TATGCCATAT    180

CATTCTCAAT ATGTACATCG ACTGAATGAA AAATTCCTGG CTGCTTTTTC ACCATGGTGT    240
```

```
ATGCCATTGA CTGATAAGAA TTATTTTGGC GGAGCCGTAT TTTCAGAAAA GGGGGAAATG      300

GTACATCAGT TGAACTATTT TGTTCCGTCT GACACTTTGG CTTTATGTAA GGTTAGCTAT      360

TATAGTTTCA CTTATCAATC AGATGGAAGC ATGTTGGTTT GGAATAATGG GGGAAGTGGC      420

AGCCCAATTG TTCAGCCTTA TACCACTTTG TATAAGGTAA CTGTTGATTC TATTTTTCCG      480

GTGTATCATT TGTTTAATGG TAATACACGA GATAAAATAG ATCATGTTCA AGGAATTGGA      540

GTTAGTGGGA ACTCTTTGGC CATAGAAACA GATTCCAGTC TCTATTTATG TTGTTATCAT      600

CCAAAGGCTC CGCATCCGTG TCCAACTTTA TGCTTTATGC GATATGATAT AAAAAATAAG      660

GTTCTTCAGG GAGTCAATTA TCCTCCTAAT GGTATTTGGG GAGGATATGT AAACCATTTG      720

AATGGTGATA TTCCAATCCG TTTCCAGTAT TCGTTTCCTC TTCAAAAGGT TTATGTATCG      780

AGTATTAGTT CTGGCGAAAT AGAGCAATTG AGAAAGTCGG GGTATATCAA TGCAAATAGT      840

GATGAAACAT TAAGGAGTAA TAAATCTGGG GATAATCCCA TTTTGATATA TTATCATTAT      900

TAATTATTTA ACAAGGAGGT AAATATGAAA AAGCTAAAAG TTTTAAATCT CTCAAAAGGT      960

GAGCAGTTTA AGATTACGGG AGGGGCTGGT AGTTGTACCG GGCCTGGTAC TTGTCGCGAA     1020

AGTAACTGTA CATGTACAGG TTGGTTAGTA AGTAACCATG CATGGACAGA AACAGATGCA     1080

AGTAAAGAAA CGCAGATGTC TTCTAACAAG GACGTTTATT CTTGGCAAGG TAACCCTGGA     1140

GCTTAGTTTA ATGTAGGTGG TAGTTTACTA CCACCTCTTT TATGTAAATT ATGAAATGAA     1200

ATCTATTATA TTTAAGGATC AATATAATTA TTGCTATTTG TATAGCTTTG GTAAGAAAAA     1260

ACTTTTACAG ATAACTCCTG AGGTTTATAA TATGCTTGAT GTTTATTGGG CTGAAGGGGA     1320

ATGTTGGGAA GGGGATAGTA ATACGGCGCG AACATGCTCT TTTTTTGAGA AATATGGTTT     1380

TTTGGATTTT GACAATATAA AAGTTGGTGC GGGTATAGAT GTAGAGGATA TAGAATATTC     1440

CATTGCAAGT GTACCAGTTA TAACATTTGA GTTGACTCAG AAATGTAATC TTGGTTGCAA     1500

ATATTGTGTG TATGGAGATC TATATGAGAC CGAAAAAGAT TGTGTTGGGA ATGAATTATC     1560

TTTTGATGTA GCAAAATCTG TCATTGATTT TTGCTTGAAT AAGGGGATGA GAAACCAATT     1620

AAGTGGTTTA AAAAGAACTA TTACAATAGG CTTTTATGGT GGAGAGCCTT TGTTGCGATT     1680

TGATTTGGTA CAGCAAATAA TATCTTATAC AAAAAGTCGG GAATCTGAGT TTCTTACATT     1740

TACTTATAAT ATGACAACTA ATGCCGTATT ACTAGATAAA TATATGGATT ATATTGTTGA     1800

GCAGGATATT TCTCTTCTTA TTAGTCTTGA TGGTGATAAG AAAGCTT               1847
```

(2) INFORMATION FOR SEQ ID NO: 6:

(i) SEQUENCE CHARACTERISTICS:
        (A) LENGTH: 1673 base pairs
        (B) TYPE: nucleic acid
        (C) STRANDEDNESS: double
        (D) TOPOLOGY: linear     (ii) MOLECULE TYPE: DNA (genomic)

(vi) ORIGINAL SOURCE:
        (A) ORGANISM: Bacteroides fragilis
        (B) STRAIN: Clinical Isolate BF-35

(xi) SEQUENCE DESCRIPTION: SEQ ID NO: 6:

```
AAGCTTTTCA TTATACCCCC CCAAGAAGGA AAGAAGGTCT TCATACCACC CAGATCATCT       60

ATAATCTGTT TCACCGCAAA TGTCTCACCC GTACGTTTAT TGTAAATGGC TGTTAATAGA      120

GGAGGCTTAG GCAGTTTACG CAGCTCCCAG TATGCCATAT ATTCATAGAC AGATAAAAAA      180

ACAAAACGCT CTGTTTCAAA AACACCGGAT ACTATATATT TGTGATCCAG CATTTTAATC      240
```

```
ATTTTTGCAT TTTCCAAGTT GCCCGATTCC CAACATTTAA AAGCATCAGA AAATAATCCA      300

TCTTCATATA GATACTGGGT AGGAAACCGT AATTCTTCAT CCAACTCCAC CACCCAGCGA      360

GGTACCAGGG AAGTGGGGGT AACAGTAAAA ACTGTATCCG TATAAAAATT ATAAAATAAG      420

GTCGTATCTT TATAGTAGCT CGTATACTTC ACACTCCCCA TGGACGGAGC GATCCCTTTC      480

CTGTTCCACG GCATCATACT GCGTTTGGCT ACAAACTCGT AATCCGTATT TATGAAATAA      540

ACCGTATCCG GAGAATTATA AAACATCAGG TTTTCTCCTG CCGGAGCAAA GCAGACCTGA      600

TTGACCAAAT GTCCAACCGG TGCAGTGTCC ATTGTTTTCT GGGTAAACCA GCTTAGCTCT      660

TTCCCCGTAC ACTTCCCCCG GTCATCATAT TCTATTATTT TAGAGGCATT CCCATAGAAA      720

TGATTATTCA AATATACTAT TTCGGCCACA TGCGCATAGA TATCTTCACA AGCCCCTTGA      780

CCCTGGCTCC CAATACGGAA CAAGAACTGC CCATTCCAAT CAAAACAATA GTTTAAGTAA      840

AATATGTATT GGGGAGAAAA GGTCAAACGC TGATAATTAC CTAACATACA ATTCGGATTC      900

GTTTCCAAAG GAATATAACT GACACTATCC ACCAGCTCCG AAAGCATCAT TTCCTCCCGA      960

ACATTCTTTA TCGCAGTTGA CAAATGAATA ATATTATCCC GAACAACAGG ATTAGGATCC     1020

ACTGTTTTTT TGTTACTACA AGCCGTGAAG CCCAATACCA TAACACCCAG TATCAATATC     1080

ATTCGCATAA AAAATTCCAT ATCCACCTAT TCTTTAAATT AGCAATTACA AGAACCGGAT     1140

TTTGCTCCTC ATCCAGTGAA TCGGTAAGCA TAACCAAACG CTCACTCACA ATTCCTCCCT     1200

TTTCTTTCTT CTCTTGAATA TATTCCTTCA ACTCAAACGG CCAAACCGAA GAAAAAAAAC     1260

TTTAGATTCA AATAATAAT TCTTCTATTT TAAAGTTGCA ATCATCAAAA TCGGATTGCT     1320

ATCCTCAGTC GCACTTTCCA AAACTCGGAT TAGCTCCTTT TTCTTGGACT CATCTATTAC     1380

GGTAGATGAT TTTATTTGGT CGATATCAAT CCAGTTCTCA TCACCGCCGG GTTCTAATAT     1440

ATCTACCCAG TATTTACCGG AAGAACGGCT GTCAACAGTA AAATCACCTC CACCTAAATC     1500

ATTATCTAAC ACAAAATCAC GTTTCATTTG GCGCAAAGGA AAGCTAAACC AGGGGACATC     1560

ACGCTCGGTT ATTGCACTTT GTCGCTTCTG CAGTCTAACA TTTCCATCTT TTTTATTATA     1620

GCAATAGGTA TATACCTCCT CGCCTTTACT ACCCACCAAA TAAATGAAAG CTT            1673
```

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Synthetic DNA"

(xi) SEQUENCE DESCRIPTION: SEQ ID NO: 7:

```
CGACGTTGTA AAACGACGGC CAGT                                              24
```

(2) INFORMATION FOR SEQ ID NO: 8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear

```
(ii) MOLECULE TYPE: other nucleic acid
     (A) DESCRIPTION: /desc = "Synthetic DNA"

(xi) SEQUENCE DESCRIPTION: SEQ ID NO: 8:

CAGGAAACAG CTATGAC                                                              17
```

PROBES FOR THE DIAGNOSIS OF INFECTIONS CAUSED BY *BACTEROIDES FRAGILIS*

FIELD OF THE INVENTION

The present invention relates to a probe which is useful for detecting and identifying *Bacteroides fragilis*, the causative bacteria of infectious diseases such as intraperitoneal infection, female genital infection, sepsis and the like.

BACK GROUND ART

Generally, the diseases caused by infection of pathogenic microorganisms are called infectious diseases. In pathology, "infection" is defined as an invasion of pathogenic microorganisms (hereinafter referred to as "bacteria") and an establishment of footholds for the growth in the host organism by the pathogenic microorganisms. Thereafter, the outbreak of the disease states caused by proliferation of the pathogenic microorganisms in vivo depends upon the relationship between the resistance of the host and the virulence of the bacteria.

Anaerobic bacteria are accounted for 20% of total bacteria strains isolated from various kinds of infectious diseases. In particular, the gram-negative anaerobicbacteria reach to 30 to 50% of the total anaerobic bacteria, and *Bacteroides fragilis* is known to be the most frequently detected strain among them.

In Bacteriology, *Bacteroides fragilis* is taxonomically classified as a nonsporing anaerobic gram-negative bacterium, which is resident within human digestive tract, external genitalia, vagina and urethra. Particularly in colon, it is present at $10^9$ to $10^{11}$ per gram of feces, and the number thereof is even higher than that of *Escherichia coli*.

*Bacterioides fragilis* is the causative bacteria of the endogenous infection of which pathological role is opportunistic. Clinically, this bacteria is detected at the higher rate in intraperitoneal infectious diseases, female genitoinfectious diseases, decubitus, diabetic ulcer, osteromyelitis, bacteremia, the infections in soft tissues of lower half of the body and the pus therefrom (Chemotherapy, Vol. 37, pp1229–1244, (1989); Rinsho Kagaku, Vol. 22, pp322–333 (1986)). Furthermore, intraperitoneal abscess is elicited as a result of the involvement of the bacteria when the perforation is caused by trauma in intestinal tracts, especially in colon, surgical procedure, ulcer, cancer, diverticulitis or appendicitis. The presence of anaerobic bacteria has been demonstrated in 90% of the cases of the intrapelvic abscess, and approximately the half of these cases may be related to *Bacterioides fragilis*. Additionally, the anaerobic bacteria are the pathogens for 5 to 10% of bacteremia, and the involvement of *Bacterioides fragilis* in these symptoms has been also known.

Nonsporing anaerobic bacteria such as *Bacteroides fragilis* are generally resistant to the antibiotics of aminoglycosides and polymyxin derivatives. Particularly, since *Bacteroides fragilis* produces β-lactamase, a tolerance for many of β-lactam agents such as penicillin and cepham have been gained. Also, a remarkable resistance against ordinarily administered antibacterial agents have been imparted, in comparison with the other anaerobic bacteria. The cephamycin-resistant and imipenem-resistant lines have been discovered as well (see, "Kagaku Ryoho no Ryoiki", Vol. 6, No. 9, 1915–1925 (1990) ). Therefore, it is extremely difficult to treat the patient, once the infection by such bacteria is established. The higher mortality has been reported, particularly in the cases that the infection lead to sepsis. Additionally, the infection of these bacteria may rather be drawn as "replacement of bacteria" through pre-administration of antibiotics before the surgical procedures.

Thus, there is a continuous need for the establishment of the method for rapid diagnosis of the infectious disease caused by *Bacteroides fragilis*, since the accurate diagnosis at an early stage of the infection and the selection of the appropriate agents are extremely crucial for the therapeutic treatment.

Infections caused by anaerobic bacteria are generally initiated by the invasion of indigenous bacteria into the tissue through a local rupture.

In the conventional diagnostic procedure, it is mandatory to: (1) analyze the clinical symptoms; (2) culture the specimen; and (3) Gram stain the bacteria which are found in the specimen, and then the therapeutic strategy is determined after these items are sufficiently examined. Actually, the following findings may tentatively suggest the suspected *Bacteroides fragilis* infection:(1) gram-negative bacteria in the specimen detected by direct Gram stain; (2) foul-smelling specimen; (3) infections found in the parts under diaphragm; (4) infectious diseases which are not effectively alleviated by any treatment using penicillin or cephalosporin derivative agent; (5) the patient suffering from diabetic ulcer, decubitus, or bacteremia. However, it is necessary to search for the correct bacteria which caused the infection, then the bacteria must be identified in order to attain the accurate diagnosis. Thereafter, the appropriate antibiotics adequate for the treatment of thus identified bacteria should be administered. Therefore, the rapid and accurate method to identify the causative bacteria has been desired in the clinical field.

In addition, the identification of the causative bacteria has been increasingly important in recent years, because of the discoveries of the several drug resistant causative bacteria.

However, the identification of the causative bacteria generally involves certain difficulties in actual clinical cases. In particular when the causative bacteria are anaerobic ones, every effort should be made in order to avoid the contamination of indigenous bacteria, and the exposure of the bacteria to air and the dryness. In more detail, identification of the causative bacteria in the specimen from the patient suspected as an anaerobic bacteria infection, the specimen such as blood, spinal fluid, pleural fluid, ascites, puncture fluid from abscess, or samples from pus or secreted materials is collected and subjected to the analysis. Since the causative bacteria are known as indigenous bacteria in human lower intestine and vagina, the specimen has to be obtained most carefully for avoiding the contamination of the indigenous bacteria, especially in the cases of the infections observed in these parts. Once the specimen is collected from the patient, it must be kept in the container designed suitable for anaerobic bacteria analysis, which immediately protects the specimen from dryness and the contact with oxygen. In general procedure to identify the causative bacteria, thus obtained specimen is observed macroscopically and examined on the presence of odor, then followed by direct Gram stain on smear, and culture in the selected medium under an aerobic condition for 48 hours. Whereas, according to this procedure, a long proliferation period of the bacteria from the specimen, and further, 3 to 4 days of incubation period would be required to attain the result of the drug sensitivity test. In addition, the cases in which *Bacteroides fragilis* can be detected as independently existing causative bacterial species are relatively rare, and 70 to 80% of the cases in which *Bacteroides fragilis* was detected were reported to be the combined cases caused by plural kinds of bacteria. In some cases, the existing *Bacteroides fragilis* may not be detected because the specimen is treated aerobically when the detection of the aerobic bacteria is intended. Additionally, in cases of the diagnosis of the patients who had already been treated with a large dose of antibiotics when the possible infection was suspected, the growth and proliferation of the bacteria may be prevented even if the bacteria are present in the specimen. Accordingly, the feasibility of successful culture of the bacteria from these specimen may become extremely low.

Furthermore, alternative subroutine methods developed heretofore may include: an instrumental analysis method of constituents of bacteria and metabolic products from bacteria (See Yoshimi Benno, "Quick identification of bacteria with gas chromatography", *Rinsho Kensa*, Vol. 29, No.12 pp.1618–1623, November 1985, Igaku Shoin.); a method utilizing a specific antibody (See Japanese Patent Provisional Publication No.60-224068.); and a hybridization method utilizing a specificity of DNA (Japanese Patent Provisional Publication No. 61-502376), however, any of which requires the steps for isolation of the bacteria, as well as the steps for culturing and growing the bacteria.

On the other hand, an established method based on the function of the phagocyte in the infectious diseases has been proposed, wherein a stained smear of buffy coat in which leukocytes constituents in the blood sample are concentrated is examined under an optical microscope. Generally speaking, the detection rate of bacteria in buffy coat specimens from adult bacteremia patients is 30% at most, which is similar to that in blood specimens from ear lobes, however, it was reported that in case that the patients are newborn children, the bacteria could be detected in seven cases in ten (70%). Therefore, information concerning the presence of bacteria in peripheral blood obtained by a microscopic prospection on a smear can provide an important guiding principle for the therapeutic treatment.

The above mentioned conventional methods necessitate the pretreatment which requires at least three to four days in total, containing one to two days for the selective isolation of bacteria from a specimen, one day for proliferating cultivation, and one or more days for operation of fixation, and the culture thereof should be continued in practice until the bacteria grow enough, therefore, the pretreatment may require one week or more days. In addition, any bacteria other than the causative bacteria may be contaminated during the culture step in some cases, and such contaminants may not be distinguished from the causative bacteria.

More importantly, as mentioned above, because many of the causative bacteria in the specimen to be proliferated and detected have been uptaked into phagocytes, and are already dead or in a bacteriostatic state due to the antibiotics administered, the number of the bacteria that can be grown may be small even under appropriate conditions for the culture of the causative bacteria, thereby, the actual detection rate of bacteria is as low as about 10% when the clinical culture specimen is employed. In the other words, for the present, 90% of the examined blood from the patient clinically suspected as suffering from the infection of *Bacteroides fragilis* could not be identified for the presence of the bacteria after all, even though the culture is continued for further one or more days.

Although the determination of the causative bacteria and selection of the antibiotics suitable for killing the bacteria as quick as possible have been eminently desired, in light of the present situation as above, the presently employed practice depends upon a therapeutic treatment which is initiated when the infection of *Bacteroides fragilis* is clinically suspected without awaiting the results of the detection of the causative bacteria. That is to say, a trial and error method has been practiced wherein an antibiotic having the effectiveness for the widest range spectra against many kinds of bacteria is administered first, and next, if the antibiotic is shown to be not effective in one or two days, another antibiotic will be tested. In such a therapeutic method, the infection of *Bacteroides fragilis* may rather be drawn as the replacement of bacteria.

Moreover, when the method for detecting the bacteria in the specimen by staining them is carried out, skilled experiences are necessary to rapidly distinguish the bacteria based merely on the shapes seen under a microscope, because the components of the host tissue may also be stained. In such cases, it may be difficult to lead a final determination.

As stated above, although the infectious diseases caused by *Bacteroides fragilis* are the diseases of which rapid and accurate diagnosis has been required, the conventional diagnosis method could not have complied with such demands.

DISCLOSURE OF THE INVENTION

The present invention was accomplished in view of the above-described problems in this art, and is directed to probes which have the specific reactivities toward DNA or RNA derived from causative bacteria of infectious diseases, specifically *Bacteroides fragilis*, and to elucidation of the nucleotide sequences of the portions of the gene essentially derived from *Bacteroides fragilis*, which should be comprised in the probe.

Accordingly, the bacterial DNA still included in the bacteria but in the process of breakdown through phagocytosis by phagocytes can be significantly detected based on its specificity using hybridization method. Therefore, rapid and accurate detection of the causative bacteria of infectious diseases can be achieved without culturing and proliferation of the bacteria. Moreover, identification of the causative bacteria can be accomplished through DNA amplification using PCR method without the hybridization process when a primer is designed with reference to the nucleotide sequence information of the probes of the present invention.

In addition, the probe used for the hybridization may be labeled with non-radioactive agent. If biotinylated probe is used for example, the detection can be carried out in a general examination laboratory not having a facility for radioisotope handling. Thus, operation for the detection can be practiced in a rapid and simple way.

BRIEF DESCRIPTION OF DRAWINGS

FIG. 1(*a*) is a drawing which shows the positions of the originated bacterial strains of the DNAs on each of the filters of dot blot hybridization, and FIG. 1(*b*) shows the results obtained by color development after the hybridization process using each probe.

BEST MODE FOR CARRYING OUT THE INVENTION

In order to explain the present invention in more detail, non-limiting Examples with respect to the probes which are derived from *Bacteroides fragilis*, causative bacteria of infectious diseases are shown below.

EXAMPLE 1

DNA Probe Derived from *Bacteroides fragilis*

(1) Preparation of DNA Probes Derived from the Bacteria *Bacteroides fragilis*

Clinical isolate of *Bacteroides fragilis* was cultured overnight in BHI (Brain Heart Infusion) medium under an anaerobic condition (5% $CO_2$), then the cultured cells were harvested, and genomic DNA was extracted therefrom in accordance with Saito-Miura modified method ("Preparation of transforming deoxyribonucleic acid by phenol treatment", *Biochem. Biophys. Acta* vol. 72, pp.619–629 (1963)) in which cell lysis step was carried out by adding N-Acetylmuramidase SG to the lysis buffer.

The extracted DNA was completely digested with restriction enzyme HindIII, then random cloned into vector pGEM-3Z. Six probes specific to *Bacteroides fragilis*, that is to say, the probes comprising DNA fragments which showed specific reactivities toward DNA included in natural *Bacteroides fragilis*, were selected from thus obtained clones.

Thereafter, the selected probes were named: probe BF-7, probe BF-17, probe BF-21, probe BF-28, probe BF-34, and probe BF-35.

(2) Studies of Species Specificity of the DNA Probes Derived from *Bacteroides fragilis*

Interactions between each probes and DNAs from several kinds of causative bacterial strains of infections were studied as follows.

First, the clinical isolates and deposited bacterial strains as listed in Table 1 below were prepared. In order to obtain the sources of Human genomic DNA in Table 1 and a control sample, leucocytes which were collected from four healthy adult men, and *Escherichia coli* K-12, JM109 transformant containing plasmid pGEM-3Z were respectively prepared.

TABLE 1

| Bacteria No. | Abbrev. | Name | Origin |
|---|---|---|---|
| 1 | BF | *Bacteroides fragilis* | Clinical Isolate |
| 2 | BT | *Bacteroides theotaiotaomicron* | Clinical Isolate |
| 3 | BV | *Bacteroides vulgutus* | Clinical Isolate |
| 4 | SA | *Staphylococcus aureus* | ATCC 25923 |
| 5 | SE | *Streptococcus epidermidis* | ATCC 12228 |
| 6 | EC | *Escherichia coli* | ATCC 25922 |
| 7 | KP | *Klebsiella pneumoniae* | Clinical isolate |
| 8 | EBC | *Enterobacter cloacae* | Clinical Isolate |
| 9 | EF | *Enterococcus faecalis* | Clinical Isolate |
| 10 | PA | *Pseudomonas aeruginosa* | ATCC 27583 |
| 11 | HI | *Haemophills influenzae* | Clinical Isolate |
| 12 | HPA | *Haemophills parainfluenzae* | Clinical Isolate |
| 13 | SP | *Streptococcus pyogenes* | Clinical Isolate |
| 14 | SAG | *Streptococcus agalactiae* | Clinical Isolate |
| 15 | SPN | *Streptococcus pneumoniae* | NYSDH DP-2 |
| 16 | HUM | U937 Human Genomic DNA | |

[Abbreviation]
NYSDH: New York State Department of Health (Albany, N.Y.,USA)

Thereafter, the DNAs included in each of the clinical isolates were extracted according to the method described in Example 1(1), then the aliquot of the extracted DNA (e.g., 10–100 ng) was spotted onto a nylon filter. After denaturation with alkali, the filter was subjected to dot blot hybridization. The human genomic DNA sample was prepared from the leukocyte obtained as mentioned previously using Saito-Miura modified method (supra). A control sample was prepared from *Escherichia coli* K-12, JM109 transformant containing plasmid pGEM-3Z using the method for preparation of plasmid DNA described in the following Example 2(1). Hybridization was then carried out overnight using a Digoxigenin-11-dUTP (BRL) labeled DNA probe which was derived from the *Bacteroides fragilis* under a hybridization condition of 45% formamide, 5×SSC, at 42° C. according to Manual by Maniatis (T. Maniatis, et al., "Molecular Cloning (A Laboratory Manual Second Edition)"., Cold Spring Harbour Laboratory (1989)).

Figure 1A:
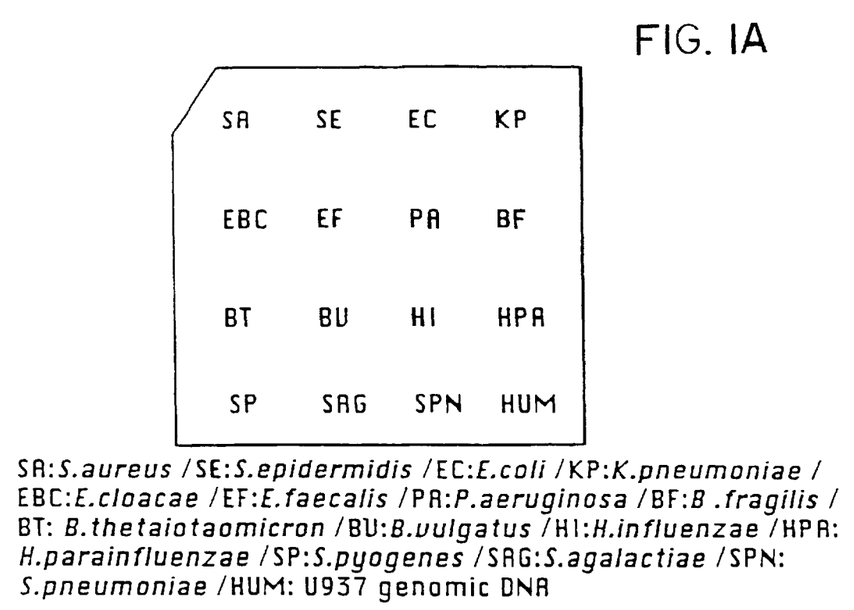
Figure 1B:
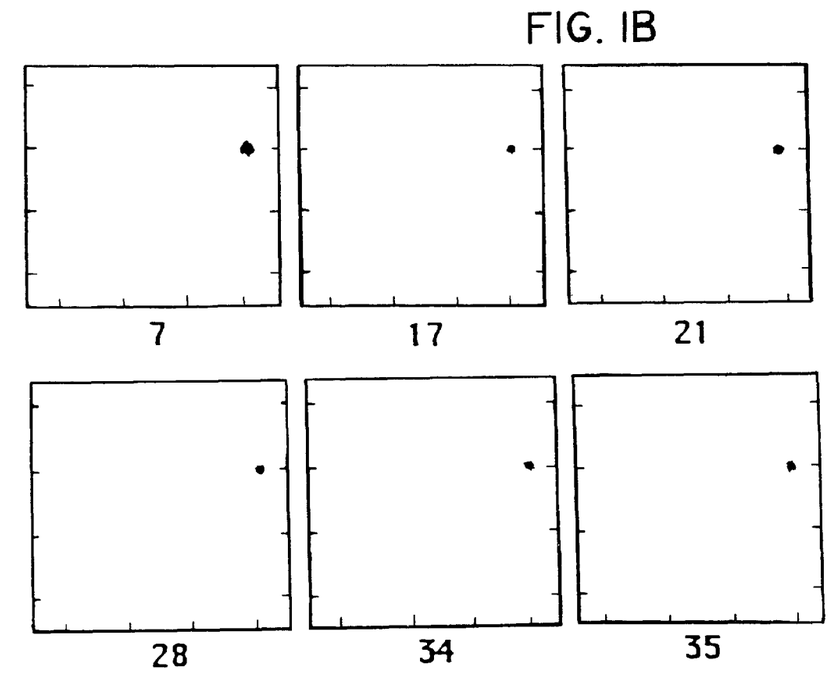

After overnight hybridization was completed, the samples were washed two times with 0.1×SSC, 0.1% SDS at 55° C. for 20 min. according to the manual, followed by color development and detection using Anti-Dig-ALP conjugates (BRL), thus results of hybridization were revealed. These results are shown in FIG. 1, wherein FIG. 1(a) illustrates the positions of the originated bacterial strains of the DNAs on each of the filters of dot blot hybridization, and FIG. 1(b) illustrates the results obtained by color development after the hybridization process using each of the above mentioned probes BF-7, BF-17, BF-21, BF-28, BF-34, and BF-35.

The experimental results with respect to the reactivities between each probes and DNAs from each of the clinical bacteria strains are shown in Table 2 below.

TABLE 2

| Bacteria | | | Probe (Denotation: BF-) | | | | | |
|---|---|---|---|---|---|---|---|---|
| No. | Abbrev. | Name | 7 | 17 | 21 | 28 | 34 | 35 |
| 1 | BF | *Bacteroides fragilis* | + | + | + | + | + | + |
| 2 | BT | *Bacteroides theotaiotaomicron* | − | − | − | − | − | − |
| 3 | BV | *Bacteroides vulgutus* | − | − | − | − | − | − |
| 4 | SA | *Staphylococcus aureus* | − | − | − | − | − | − |
| 5 | SE | *Streptococcus epidermidis* | − | − | − | − | − | − |
| 6 | EC | *Escherichia coli* | − | − | − | − | − | − |
| 7 | KP | *Klebsiella pneumoniae* | − | − | − | − | − | − |
| 8 | EBC | *Enterobacter cloacae* | − | − | − | − | − | − |
| 9 | EF | *Enterococcus faecalis* | − | − | − | − | − | − |
| 10 | PA | *Pseudomonas aeruginosa* | − | − | − | − | − | − |
| 11 | HI | *Haemophills influenzae* | − | − | − | − | − | − |
| 12 | HPA | *Haemophills parainfluenzae* | − | − | − | − | − | − |
| 13 | SP | *Streptococcus pyogenes* | − | − | − | − | − | − |
| 14 | SAG | *Streptococcus agalactiae* | − | − | − | − | − | − |
| 15 | SPN | *Streptococcus pneumoniae* | − | − | − | − | − | − |
| 16 | HUM | U937 Human Genomic DNA | − | − | − | − | − | − |

[Remarks]
+: hybridization signal detected
−: hybridization signal not detecte

As is evident from the Tables 1 and 2 above, all of the present probes showed reactivities only to the DNA derived from *Bacteroides fragilis*, while no reactivity (i.e., hybrid formation) was observed toward the DNAs from the every other bacterial species in the genus Bacteroides, as well as the DNAs from the bacterial species other than genus Bacteroides. Thus, the specificity of the probes was demonstrated.

EXAMPLE 2

Analysis of the Base Sequence

Each of the base sequences of the DNA probes (six probes in total) of which species specificity was demonstrated in Example 1 as above was determined according to the following procedure.

(1) Preparation of Plasmid DNA

*Escherichia coli* K-12, JM109 transformant, wherein the sub-cloned insert fragment (to be sequenced) is contained in pGEM-3Z (Promega), was inoculated into 5 ml of Luria-Bactani Medium (bacto-tryptone, 10 g/1 L; bacto-yeast extract, 5 g/1 L; NaCl, 10 g/1 L; adjusted pH to 7.0 with 5 N NaOH)and cultured overnight.

The culture liquid mixture was centrifuged (5,000 rpm, 5 min.) to collect the bacteria. One hundred $\mu$l of a solution of 50 mM glucose/50 mM Tris-HCl (pH8.0)/10 mM EDTA containing 2.5 mg/ml of lysozyme (Sigma) was added to the precipitate, and left at room temperature for 5 minutes. To the suspension, 0.2M NaOH solution containing 1% of sodium dodecyl sulfate (Sigma) was added and mixed. One hundred and fifty $\mu$l of 5M potassium acetate aqueous solution (pH 4.8) was further added thereto and mixed, then cooled on ice for 15 minutes.

The supernatant collected by centrifugation (15,000 rpm, 15 min.) of the mixture was treated with phenol/CHCl$_3$, and ethanol of two times by volume was added thereto, then the precipitate was again obtained by centrifugation (12,000 rpm, 5 min.). This precipitate was dissolved in 100 $\mu$l of a solution of 10 mM Tris-HCl (pH7.5)/0.1 mM EDTA, followed by addition of 10 mg/ml RNase A (Sigma) solution, then the mixture was left at room temperature for 15 minutes.

Three hundred $\mu$l of 0.1M sodium acetate aqueous solution (pH 4.8) was added to this mixture and treated with phenol/CHCl$_3$, then the precipitate was obtained therefrom by adding ethanol to the supernatant. This precipitate was dried and dissolved in 10 $\mu$l of distilled water to give a DNA sample.

(2) Pretreatment for Sequencing

Pretreatment for sequencing was performed with Auto-ReadT™ Sequencing Kit (Pharmacia).

Concentration of DNA to be employed as a template was adjusted to 5–10 $\mu$g in 32 $\mu$l of a solution. Thirty two $\mu$l of the template DNA solution was transferred to a mini-tube (1.5 ml, Eppendolf), and added thereto 8 $\mu$l of 2M NaOH aqueous solution, then mixed gently. After instant centrifugation, it was left at room temperature for 10 minutes.

Seven $\mu$l of 3M sodium acetate (pH 4.8) and 4 $\mu$l of distilled water were added, followed by 120 $\mu$l of ethanol, and after mixing, the mixture was left for 15 minutes on ethanol/dry ice. DNA which was precipitated by centrifugation for 15 minutes was collected, and the supernatant was removed carefully. The precipitate thus obtained was washed with 70% ethanol and centrifuged for 10 minutes. Then, after the supernatant was carefully removed again, the precipitate was dried under the reduced pressure.

The precipitate was dissolved in 10 $\mu$l of distilled water, then 2 $\mu$l of fluorescent primer (0.42 A$_{260}$ unit/ml, 4–6 pmol [Fluorescent Primer; Universal Primer: 5'-Fluorescein-d[CGACGTTGTAAAACGACGGCCAGT (SEQ ID NO: 7)]-3' (1.6 pmol/$\mu$l, 0.42 A$_{260}$ unit/ml); Reverse Primer: 5'-Fluorescein-d[CAGGAAACAGCTATGAC (SEQ ID NO: 8)]-3' (2.1 pmol/$\mu$l, 0.42 A$_{260}$ unit/ml), and 2 $\mu$l of annealing buffer was added thereto, and mixed gently.

After instant centrifugation, the mixture was heat-treated at 65° C. for 5 minutes and rapidly transferred to a circumstance of 37° C. and kept the temperature for 10 minutes. After keeping the temperature, it was left at room temperature for more than 10 minutes, and centrifuged instantly.

Then, the sample was prepared by adding thereto 1 $\mu$l of elongation buffer and 3 $\mu$l of dimethyl sulfoxide.

Four mini-tubes have been identified with one of the marks of "A", "C", "G" and "T", and, according to the respective mark, 2.5 $\mu$l of A Mix (dissolved ddATP with dATP, dCTP, c$^7$dGTP and dTTP), C Mix (dissolved ddCTP with dATP, dCTP, c$^7$dGTP and dTTP), G Mix (dissolved ddGTP with dATP, dCTP, c$^7$dGTP and dTTP), or T Mix (dissolved ddTTP with dATP, dCTP, c$^7$dGTP and dTTP) was poured into each identified tube. Each solution was preserved on ice until use, and was incubated at 37° C. for one minute or more before use.

Two $\mu$l of diluted T7 DNA polymerase (Pharmacia; 6–8 units/2 $\mu$l) was added to the DNA sample, and completely mixed by pipetting or mixing it gently.

Immediately after completion of the mixing, the mixed solution was distributed to 4.5 $\mu$l of the four types of the solutions respectively which had been incubated at the same temperature. Fresh tips were used for each distribution.

The solutions were kept for 5 minutes at 37° C., then 5 $\mu$l of termination solution was added to each reaction mixture.

Fresh tips were also used for this step. Immediately after incubating the solution for 2–3 minutes at 90° C., it was cooled on ice. Four to six $\mu$l of the solution per lane was applied for the electrophoresis.

(3) Sequencing on Base Sequences

Sequencing on the base sequences of the probes disclosed in Examples 1 and 2, having the specificity toward DNA from *Bacteroides fragilis* was performed using A.L.F. DNA Sequencer System (Pharmacia) under a condition of the electrophoresis process of 45° C. for 6 hours. Primers were serially designed based on the sequences elucidated from each of the upstream and downstream sequences, and the above described procedures were repeated.

Consequently, all of the entire base sequences of the probe BF-7 (SEQ ID NO: 1), probe BF-17 (SEQ ID NO: 2), probe BF-21 (SEQ ID NO: 3), probeBF-28 (SEQ ID NO: 4), probe BF-34 (SEQ ID NO: 5) and probe BF-35 (SEQ ID NO: 6) were elucidated.

[Industrial Applicability]

Using the probes according to the present invention, the causative bacteria which were incorporated into the phagocytes can be rapidly and accurately identified directly without proliferation of the bacteria by for example, a hybridization method. In other words, the diagnosis wherein the probes of the present invention are used enables the identification of the causative bacteria with single specimen, further, the necessary time for diagnosis can be diminished to approximately 1 to 2 days, while the conventional method with low detection rate requires 3–4 days, and the resulting detection rate is remarkably improved. Therefore, the present invention provides guiding principles of the therapeutic treatment for the infectious diseases caused by *Bacteroides fragilis*, in addition, the effective treatment in an early stage of the infection can be adopted to the patients, which may lead to a reduction of the mortality.

Additionally, in accordance with the present invention wherein the base sequences of the probes which specifically react with the DNA derived from *Bacteroides fragilis* among other several causative bacteria of the infectious diseases were elucidated, artificial preparation of these probes has become feasible. Moreover, a part of the information of the base sequences provided herein may be utilized to produce primers, which are useful for rapid diagnosis through amplification of DNA of causative bacteria contained in the clinical specimen by a PCR method.

Furthermore, the rapid identification of the causative bacteria may be carried out by comparing the base sequences of the genomic DNA from the clinical specimen with the base sequences provided by the present invention.

As stated above, the present invention provides the desired probe for the diagnosis of the infections, besides, outstanding utilities as guiding principles for the manufacture of the primers for PCR as well as standard sequences which are suitable for the comparison of genomic DNA contained in the clinical specimen can be expected. Moreover, the present invention may exert beneficial effects by providing valuable clues for preparation and development of the novel probes which specifically react with the DNA from the causative bacteria of the infectious diseases.

Further, the base sequence disclosed in the present application was obtained by random-cloning of the genomic DNA from the clinical isolates, therefore, the utilities of the base sequences of the present invention should be encompassed to the complementary strand thereof.

Additionally, it may be presumed that DNA obtained from the wild strains might contain the mutated portion. However, as apparent from the disclosure of the Examples above, such mutated DNA portion would not affect the utilities which should be derived from the present invention, comprising the specificity of the probe of the present invention in the hybridization procedure for the diagnosis of the infections, and usages of the information on the base sequences disclosed in the present application for designing the primer to be employed for the PCR techniques with the aim of a rapid diagnosis of the infections.

What is claimed is:

1. A purified nucleic acid useful as a probe for diagnosing infectious diseases consisting of a nucleotide sequence selected from the group consisting of SEQ ID NOS: 1, 2, 3, 4, 5, and 6, and the complements of SEQ ID NOS: 1, 2, 3, 4, 5, and 6.

2. A purified nucleic acid according to claim 1 consisting of the nucleotide sequence set forth in SEQ ID NO: 1, or the complement of SEQ ID NO: 1.

3. A purified nucleic acid according to claim 1 consisting of the nucleotide sequence set fourth in SEQ ID NO: 2, or the complement of SEQ ID NO: 2.

4. A purified nucleic acid according to claim 1 consisting of the nucleotide sequence set fourth in SEQ ID NO: 3, or the complement of SEQ ID NO: 3.

5. A purified nucleic acid according to claim 1 consisting of the nucleotide sequence set forth in SEQ ID NO: 4, or the complement of SEQ ID NO: 4.

6. A purified nucleic acid according to claim 1 consisting of the nucleotide sequence set forth in SEQ ID NO: 5, or the complement of SEQ ID NO: 4.

7. A purified nucleic acid according to claim 1 consisting of the nucleotide sequence set forth in SEQ ID NO: 6, or the complement of SEQ ID NO: 6.

8. A purified polynucleotide consisting of a nucleotide sequence selected from the group consisting of SEQ ID NOS: 1, 2, 3, 4, 5, and 6, and the complements of SEQ ID NOS: 1, 2, 3, 4, 5, and 6.

9. A probe for the diagnosis of infectious disease comprising a purified nucleic acid according to claim 1, said nucleic acid further comprising a detectable label.

10. A probe for the diagnosis of infectious disease comprising a purified polynucleotide according to claim 8, said polynucleotide further comprising a detectable label.

11. A purified nucleic acid useful as a probe for diagnosing infectious disease consisting of a nucleotide sequence selected from the group consisting of SEQ ID NOS: 1, 2, 3, 4, 5, and 6, and the complements of SEQ ID NOS: 1, 2, 3, 4, 5, and 6, wherein said nucleic acid hybridizes a genomic DNA of *bacteroides fragilis*, but fails to hybridize to genomic DNA of *bacteroides theotaiotaomicron* and *bacteroides vulgutus*, under the following hybridization and washing conditions: hybridization overnight at 42° C. is a hybridization solution comprising 45% formamide and 5×SSC; and washing twice for 20 minutes at 55° C. in washing solution comprising 0.1×SSC and 0.1% SDS.

12. A purified nucleic acid according to claim 11 consisting of the nucleotide sequence set forth in SEQ ID NO: 1, of the complement of SEQ ID NO: 1.

13. A purified nucleic acid according to claim 11 consisting of the nucleotide sequence set forth in SEQ ID NO: 2, or the complement of SEQ ID NO: 2.

14. A purified nucleic acid according to claim 11 consisting of the nucleotide sequence set forth in SEQ ID NO: 3, or the complement of SEQ ID NO: 3.

15. A purified nucleic acid according to claim 11 consisting of the nucleotide sequence set forth in SEQ ID NO: 4, or the complement of SEQ ID NO: 4.

16. A purified nucleic acid according to claim 11 consisting of the nucleotide sequence set forth in SEQ ID NO: 5, of the complements of SEQ ID NO: 5.

17. A purified nucleic acid according to claim 11 consisting of the nucleotide sequence set forth in SEQ ID NO: 6, or the complement of SEQ ID NO: 6.

18. A purified polynucleotide useful as a probe for diagnosing infectious disease consisting of a nucleotide sequence selected from the group consisting of SEQ ID NOS: 1, 2, 3, 4, 5, and 6, and the complements of SEQ ID NOS: 1, 2, 3, 4, 5, and 6, wherein said nucleic acid hybridizes to genomic DNA of *bacteroides fragilis*, but fails to hybridize to genomic DNA of *bacteriodes theotaiotamicron* and *bacteriodes vulgutus*, under the following hybridization and washing conditions: hybridization overnight at 42° C. in hybridization solution comprising 45% formamide and 5×SSC; and washing twice for 20 minutes at 55° C. in a washing solution comprising 0.1×SSC and 0.1% SDS.

19. A probe for the diagnosis of infectious disease comprising the purified nucleic acid according to claim 11, said nucleic acid further comprising a detectable label.

20. A probe for the diagnosis of infectious disease comprising the purified polynucleotide according to claim 18, said polynucleotide further comprising a detectable label.

\* \* \* \* \*

UNITED STATES PATENT AND TRADEMARK OFFICE
CERTIFICATE OF CORRECTION

PATENT NO. : 6,265,568 B1
DATED : July 24, 2001
INVENTOR(S) : Hiroshi Ueyama, Kanako Abe, Hiroyuki Keshi and Akio Matsuhisa It is certified that error appears in the above-identified patent and that said Letters Patent is hereby corrected as shown below:

Column 23, claim 11,
Line 46, "disease" should be -- diseases --.
Line 49, "hybridizes a genomic" should be -- hybridizes to genomic --.

Column 24, claim 11,
Line 1, "42°C is a hybridization" should be -- 42°C in a hybridization --.
Line 3, "in washing solution" should be -- in a washing solution --.

Column 24, claim 18,
Line 43, "42°C in hybridization" should be -- 42°C in a hybridization --.

Signed and Sealed this

Twenty-sixth Day of March, 2002

Attest:

JAMES E. ROGAN
*Attesting Officer*      *Director of the United States Patent and Trademark Office*